US012426556B2

(12) United States Patent
Hazlebeck et al.

(10) Patent No.: US 12,426,556 B2
(45) Date of Patent: Sep. 30, 2025

(54) SYSTEMS AND METHODS FOR ALGAE CULTIVATION USING DIRECT AIR CAPTURE

(71) Applicant: Global Algae Technology, LLC, San Diego, CA (US)

(72) Inventors: David A. Hazlebeck, El Cajon, CA (US); William Rickman, Lebanon, TN (US); Paul Hazlebeck, El Cajon, CA (US)

(73) Assignee: Global Algae Technology, LLC, San Diego, CA (US)

( * ) Notice: Subject to any disclaimer, the term of this patent is extended or adjusted under 35 U.S.C. 154(b) by 1137 days.

(21) Appl. No.: 17/346,030

(22) Filed: Jun. 11, 2021

(65) Prior Publication Data

US 2021/0386029 A1 Dec. 16, 2021

Related U.S. Application Data

(60) Provisional application No. 63/038,021, filed on Jun. 11, 2020.

(51) Int. Cl.

| | |
|---|---|
| ***A01G 33/00*** | (2006.01) |
| ***A01G 7/02*** | (2006.01) |
| ***C12M 1/00*** | (2006.01) |
| ***C12N 1/12*** | (2006.01) |
| ***C12N 13/00*** | (2006.01) |

(52) U.S. Cl.

CPC ............... *A01G 33/00* (2013.01); *A01G 7/02* (2013.01); *C12M 21/02* (2013.01); *C12M 23/18* (2013.01); *C12M 27/20* (2013.01); *C12N 1/12* (2013.01); *C12N 13/00* (2013.01)

(58) Field of Classification Search

CPC ......... A01G 33/00; A01G 7/02; C12M 21/02; C12M 23/18; C12N 1/12; C12N 13/00

See application file for complete search history.

(56) References Cited

U.S. PATENT DOCUMENTS

| | | | | |
|---|---|---|---|---|
| 10,907,127 | B2 * | 2/2021 | Hazlebeck | C12M 23/18 |
| 2014/0273170 | A1 * | 9/2014 | Osterloh | C12M 27/00 435/257.1 |
| 2015/0182923 | A1 | 7/2015 | Malkiel et al. | |
| 2017/0318771 | A1 * | 11/2017 | Hazlebeck | A01G 33/00 |

OTHER PUBLICATIONS

International Search Report of International Application No. PCT/US21/37106 mailed Sep. 24, 2021, 2 pages.
Written Opinion of International Application No. PCT/US21/37106 mailed Sep. 24, 2021, 4 pages.

* cited by examiner

*Primary Examiner* — Mary Maille Lyons
(74) *Attorney, Agent, or Firm* — Quarles & Brady LLP

(57) ABSTRACT

Embodiments of the disclosure provide systems and methods for supplying an algae cultivation fluid with nutrients (e.g., carbon dioxide and nitrogen) directly from the atmosphere. Supplying nutrients directly from the atmosphere reduces operational costs and environmental impacts, as well as provides greater flexibility in locating algae farms.

26 Claims, 8 Drawing Sheets

SYSTEMS AND METHODS FOR ALGAE CULTIVATION USING DIRECT AIR CAPTURE

CROSS REFERENCE TO RELATED APPLICATIONS

This application claims priority to and the benefit of U.S. Patent Application No. 63/038,021, filed Jun. 11, 2020, the contents of which are herein incorporated by reference.

GOVERNMENT SUPPORT

This invention was made with government support under Grant No. DE-EE0008639 and DE-EE0008516 awarded by the U.S. Department of Energy. The government has certain rights in the invention.

BACKGROUND

Algae utilizes the supply of nutrients for cultivation. Algae utilize photosynthesis to fix $CO_2$ for growth. Typically, high intensity cultivation in an algae farm utilizes addition of $CO_2$ in some form to support a high productivity. In some cases, pure $CO_2$ is bubbled into the raceways to support high rates of photosynthesis. This approach enables locating algae farms almost anywhere, but the cost of buying the $CO_2$ is high, typically over $100 per ton in 2020 dollars. Utilizing a moderately concentrated $CO_2$ source, e.g. 1% to 20% $CO_2$ by volume, such as generated by combustion flue gas is less expensive than purchasing pure $CO_2$ but limits the algae farm to being located near a source of $CO_2$.

Algae utilize a nitrogen source for growth as well. Some blue-green algae or cyanobacteria can fix $N_2$ directly from the atmosphere; however, the absorption rate of $N_2$ becomes rate limiting during periods of high productivity. In column or flat panel closed photobioreactors, a high rate of air bubbling is used to supply enough $N_2$ absorption to support high productivity. Typical raceway cultivation does not have the intense air mixing that is present in these systems, so high productivity is not attained with $N_2$ absorption from the atmosphere as the nitrogen source for growth.

SUMMARY OF THE INVENTION

The present disclosure provides systems and methods for supplying an algae cultivation fluid with nutrients (e.g., carbon dioxide and nitrogen) directly from the atmosphere or air. Supplying nutrients directly from the atmosphere reduces operational costs and environmental impacts, as well as provides greater flexibility in locating algae farms.

The systems and methods provided herein provide advantages over existing systems including, but not limited to, increased biomass productivity (g/m$^2$d) of algae that can be supported with direct air capture of carbon dioxide for pH operating ranges of 9.0 or greater; increased biomass productivity that can be supported with direct air capture of nitrogen allowing for higher carbon dioxide capture at lower pH values (e.g., at pH values lower than 10.2); increased range of species that can be grown using direct air capture of carbon dioxide due to expanded pH ranges; reduced energy use required for direct air capture of nitrogen and carbon dioxide in algae cultivation fluids; increased response and recovery to process perturbations; and reduced impact of perturbations on the biomass productivity.

In some configurations, the present disclosure provides a method comprising the steps of culturing algae in at least one channel having a sloped bottom surface, a pair of opposing side walls, and an algae cultivation fluid disposed in the at least one channel. The method further includes applying bore waves through the algae cultivation fluid at a bore wave frequency sufficient to disrupt an air-liquid interface of the algae cultivation fluid to induce direct absorption of atmospheric carbon dioxide or atmospheric nitrogen from air into the algae cultivation fluid, where a majority of the carbon or nitrogen in the algae is from the atmospheric carbon dioxide or atmospheric nitrogen.

In some embodiments, the bottom surface of the channel is sloped.

In some embodiments, the slope of the bottom surface is less than 0.5%.

In some embodiments, the method includes passing the bore waves through one or more air-liquid mixing device configured within the at least one channel.

In some embodiments, the at least one channel include from one air-liquid mixing device for every 300 ft$^2$ of surface of the at least one channel to one air-liquid mixing device for every 400,000 ft$^2$ of surface of the at least one channel.

In some embodiments, the one or more the air-liquid mixing devices are powered by the flow of the bore wave. In some embodiments, a rate of air-liquid mixing is adjusted during the cultivation to reduce the energy consumption. In some embodiments, solar energy is used to power the at least one air-liquid mixing device, and wherein a rate of air-liquid mixing is greater during times of higher solar radiation relative to times of lower solar radiation.

In some embodiments, the air-liquid mixing device generates air bubbles in the algae cultivation fluid. The bubble generation rate may be increased when the bore wave passes the air-liquid mixing device, and may be decreased during the period in between the bore waves.

In some embodiments, the at least one channel has a surface area of at least 100 ft$^2$. In some embodiments, the at least one channel has a surface area from 10,000 ft$^2$ to 20,000,000 ft$^2$. In some embodiments, the bore wave frequency, intensity, or a combination thereof is adjusted to obtain a minimum bicarbonate concentration in the algae cultivation fluid from 1 mM to 150 mM, or from 10 mM to 150 mM, or from 50 mM to 150 mM. In some embodiments, an equivalent bicarbonate concentration of sodium ions in the algae cultivation fluid is from 10 mM to 500 mM.

In some embodiments, an equivalent bicarbonate concentration of sodium ions in the algae cultivation fluid and the bore wave frequency are selected to maintain a difference between a maximum and minimum pH during day light hours of less than 0.8 pH units, or less than 0.7 pH units, or less than 0.5 pH units, or less than 0.4 pH units, or less than 0.3 pH units.

In some embodiments, the bore wave frequency, intensity, or a combination thereof is adjusted to maintain a pH in the algae cultivation fluid of less than 11, or less than 10.6, or less than 10.2.

In some embodiments, the bore wave frequency is adjusted by displacing a gate in a bore wave generator. In some embodiments, the gate is displaced at a frequency from 10 seconds to 300 seconds to apply the bore waves through the algae cultivation fluid. In some embodiments, the bore wave intensity is adjusted by the height of the algae cultivation fluid behind a gate in a bore wave generator. In some embodiments, the height of the algae cultivation fluid is adjusted by the rate of filling of an area behind the gate with the algae cultivation fluid.

In some embodiments, the method includes measuring at least one process parameter in the algae cultivation fluid, and adjusting the bore wave frequency, intensity, or a combination thereof based on the at least one parameter or rate of change of the at least one parameter. In some embodiments, the parameter is selected from the group consisting of a pH, a dissolved oxygen content, a bicarbonate concentration, a nitrogen concentration, solar intensity, algae growth rate, turbidity, optical density, and temperature. In some embodiments, the method includes adjusting the bore wave frequency, intensity or a combination thereof to maintain a desired set-point of the at least one process parameter.

In some configurations, the present disclosure provides an algae cultivation system comprising at least one channel having a sloped bottom surface, a pair of opposing side walls, and an algae cultivation fluid disposed in the at least one channel. In some embodiments, the sloped bottom surface has a drop-off that interrupts the sloped bottom surface. In some embodiments, the drop off has a height that is greater than a depth of the algae cultivation fluid in the at least one channel.

In some embodiments, the height of the drop off is from 1 cm to 20 cm greater than the depth of the algae cultivation fluid in the at least one channel. In some embodiments, the slopped bottom surface has a slope percentage from 0% to 1%. In some embodiments, the drop-off includes at least one weir. In some embodiments, the weir has a height that extends at least 50% of a depth of the algae cultivation fluid directly above the drop-off.

In some configurations, the present disclosure provides an algae cultivation system. The algae cultivation system includes at least one channel having a sloped bottom surface, a pair of opposing side walls, and an algae cultivation fluid disposed in the at least one channel, the at least one channel having a cross-sectional area. The system further includes a narrowed region in the at least one channel, the narrowed region having a cross-sectional area that is smaller than the cross-sectional area of the at least one channel. In some embodiments, the system further includes a diffuser positioned in the narrowed region. The diffuser is coupled to a pipe that extends above an air-liquid interface of the algae cultivation fluid to place the diffuser in fluid communication with air, the diffuser having a plurality of apertures that are configured to dispense the air into the algae cultivation fluid.

In some embodiments, the opposing side walls have a segment that protrudes inward within the at least one channel to form the narrowed region. In some embodiments, the sloped bottom surface includes a protrusion that extends vertically upwards to form the narrowed region. In some embodiments, the sloped bottom surface includes a drop-off that forms the narrowed region.

In some configurations, the present disclosure provides an algae cultivation system. The algae cultivation system includes at least one channel having a sloped bottom surface extending from a high end to a low end, a pair of opposing side walls, and an algae cultivation fluid disposed in the at least one channel. The system includes a sump connected to a low end of the sloped bottom surface, where the sump includes opposing sump walls connected to a sump bottom. The system includes a dividing wall the separates the sump into a fluid collection side and an air-lift side. A diffuser is positioned on the air-lift side and in fluid communication with an air transfer device that dispenses air into the diffuser. The diffuser has a plurality of apertures that are configured to dispense the air into the algae cultivation fluid and transport the algae cultivation fluid from a bottom end of the sump to a holding section configured above the sump.

In some configurations, the present disclosure provides an algae harvesting system comprising a housing having a liquid inlet, a retentate outlet, a permeate outlet, a gas inlet, and a gas outlet. The housing comprises a membrane that separates the housing into a permeate side and a retentate side. The algae harvesting system further includes an algae cultivation system in fluid communication with the liquid inlet, the algae cultivation system comprising algae cultivation fluid and algae, where the membrane separates the algae cultivation fluid and algae into an algae paste that exits the housing through the retentate outlet and a permeate fluid that exits the housing through the permeate outlet. The algae harvesting system further includes a gas conduit that places the housing in fluid communication with a gas supply unit via the gas inlet, the gas supply unit configured to transport air into the gas inlet and enrich the permeate fluid with carbon dioxide or nitrogen to form a bicarbonate- or nitrogen-rich permeate fluid.

In some configurations, the present disclosure provides a method including the steps of feeding algae cultivation fluid and algae into a liquid inlet of an algae cultivation harvester, separating the algae cultivation fluid and the algae into an algae paste and a permeate stream by contacting the algae cultivation fluid and algae to a membrane in the algae cultivation harvester, and feeding air into the algae cultivation harvester to enrich the permeate stream with carbon dioxide or nitrogen to form a bicarbonate or nitrogen rich permeate stream.

In some configurations, the present disclosure provides a method including the steps of culturing a nitrogen fixing algae in at least one channel having a bottom surface, opposing side walls coupled to the bottom surface, and an algae cultivation fluid disposed in the at least one channel, and applying bore waves through the algae cultivation fluid at a bore wave frequency sufficient to disrupt an air-liquid interface of the algae cultivation fluid to induce direct absorption of atmospheric nitrogen from air into the algae cultivation fluid, where a majority of the nitrogen in the algae is from the atmospheric nitrogen.

In some configurations, the present disclosure provides a method including culturing algae in at least one channel having a bottom surface, opposing side walls coupled to the bottom surface, and an algae cultivation fluid disposed in the at least one channel, and where the at least one channel contains at least one air-liquid mixing device that induces direct absorption of atmospheric nitrogen or carbon dioxide from air into the algae cultivation fluid, where the air-liquid mixing device is operated such that the majority of the nitrogen or carbon in the algae is from the atmospheric nitrogen or atmospheric carbon dioxide.

These and other advantages and features of the invention will become more apparent from the following detailed description of the preferred embodiments of the invention when viewed in conjunction with the accompanying drawings.

DETAILED DESCRIPTION

As noted above, high levels of algae biomass productivity ($g/m^2d$) utilize supplementation of gaseous nutrients, such as carbon dioxide and nitrogen, for cultivation. Typically, cultivation farms utilize the addition of concentrated carbon dioxide or flue gas as a source for carbon dioxide. These approaches increase operating costs of the cultivation farm, and in the case of flue gas utilization, can limit the location of the farm.

The present disclosure addresses the aforementioned drawbacks by providing systems and methods for supplying an algae cultivation fluid 12 with nutrients (e.g., carbon dioxide and nitrogen) directly from air (e.g., gases within the atmosphere). In some embodiments, the present disclosure provides systems and methods that may maintain a sufficient concentration of carbon dioxide and nitrogen in an algae cultivation fluid 12 for biomass productivity of at least 8 $g/m^2d$ using direct capture of atmospheric carbon dioxide and atmospheric nitrogen. In some embodiments, the systems and methods provided herein are performed without applying, supplementing, or treating an algae cultivation fluid 12 with concentrated carbon dioxide, concentrated nitrogen, and/or flue gas.

As used herein, the terms "air" and "atmosphere" may refer to gases surrounding the earth, which may vary regionally, and are a function of various factors, such as temperature and pressure. As one example, the terms "air" and "atmosphere" may refer to a gaseous composition composed, in a dry volume percentage (vol %), of about 78 vol % nitrogen, about 20.9 vol % oxygen, about 0.9 vol % argon, about 0.04 vol % carbon dioxide, and other elements and compounds such as helium, methane, krypton, hydrogen, nitrous oxide, xenon, ozone, carbon monoxide, sulfur dioxide, nitrogen dioxide, and ammonia. As used herein, the term "atmospheric carbon dioxide" may refer to carbon dioxide derived from air, and the term "atmospheric nitrogen" refers to nitrogen derived from air.

As used herein, the terms "concentrated carbon dioxide" and "concentrated nitrogen" refer to a carbon dioxide or nitrogen source containing between 20 vol % to 100 vol % carbon dioxide or nitrogen, based on the total volume of the source. Example concentrated carbon dioxide or nitrogen sources included pressurized vessels containing the specified volume percentage of carbon dioxide or nitrogen. As used herein, the term "flue gas" refers to exhaust gas exiting a pipe or channel from a chemical process or plant (e.g., furnace, boiler, steam generator), which is composed of from 1 vol % to 20 vol % carbon dioxide and at least 65 vol % nitrogen.

Figure 1:
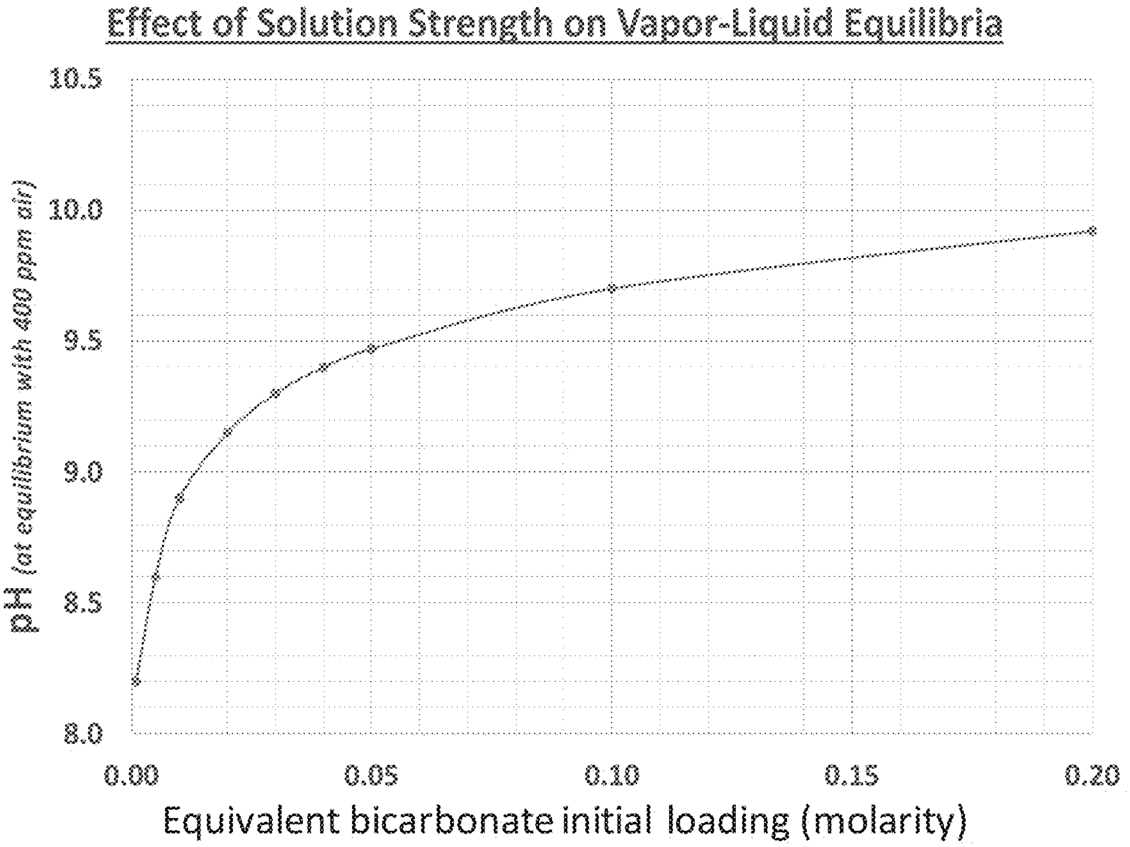
FIG. 1 is an exemplary graph of vapor-liquid equilibria between carbon dioxide and an algae cultivation fluid.

I. Carbon Dioxide-Algae Cultivation Fluid Equilibria:

FIG. 1 illustrates the pH at which the partial pressure of carbon dioxide from algae cultivation fluid 12 is in equilibrium with the partial pressure of air as a function of the equivalent bicarbonate concentration. As used herein, the term "equivalent bicarbonate" or "equivalent bicarbonate concentration" may refer to the molarity of sodium ions that are paired with bicarbonate and/or carbonate ions to provide a concentration of carbon dioxide dissolved in the algae cultivation fluid 12. As shown in FIG. 1, if the media pH is higher than the equilibrium curve at the equivalent bicarbonate loading in the algae cultivation fluid 12, then there is a driving force for carbon dioxide capture from the air, and the algae cultivation fluid 12 will absorb atmospheric carbon dioxide.

Operating under high pH allows for the spontaneous absorption of carbon dioxide into the algae cultivation fluid 12. Although this is an effective technique for small scale cultivation farms (e.g., less than 2 square feet), as the size of the cultivation farm increases to larger scales (e.g., greater than 10 square feet), the spontaneous diffusion of carbon dioxide is diffusion limited, and becomes insufficient for providing algae with proper levels of carbon dioxide and nitrogen for large scale production. That is, the spontaneous diffusion of carbon dioxide into the cultivation media, along with standard paddle wheel circulation, for cultivation farms larger than 10 square feet is insufficient to maintain an average equivalent bicarbonate level that is suitable for biomass productivity of greater than 8 $g/m^2d$ of algae, unless the pH is very high, e.g., greater than 10.8, such that there are few algae that can grow at this productivity.

The present disclosure provides systems and methods for improving direct air capture of atmospheric carbon dioxide and atmospheric nitrogen into algae cultivation fluid 12. In some embodiments, the algae cultivation systems provided herein allow for sufficient direct absorption of atmospheric carbon dioxide to maintain an average equivalent bicarbonate concentration of at least 1 mM in the algae cultivation fluid 12, have a biomass productivity of at least 8 $g/m^2d$, and maintain these specified parameters while operating within a raceway and/or channel size of at least 10 square feet.

Figure 2:
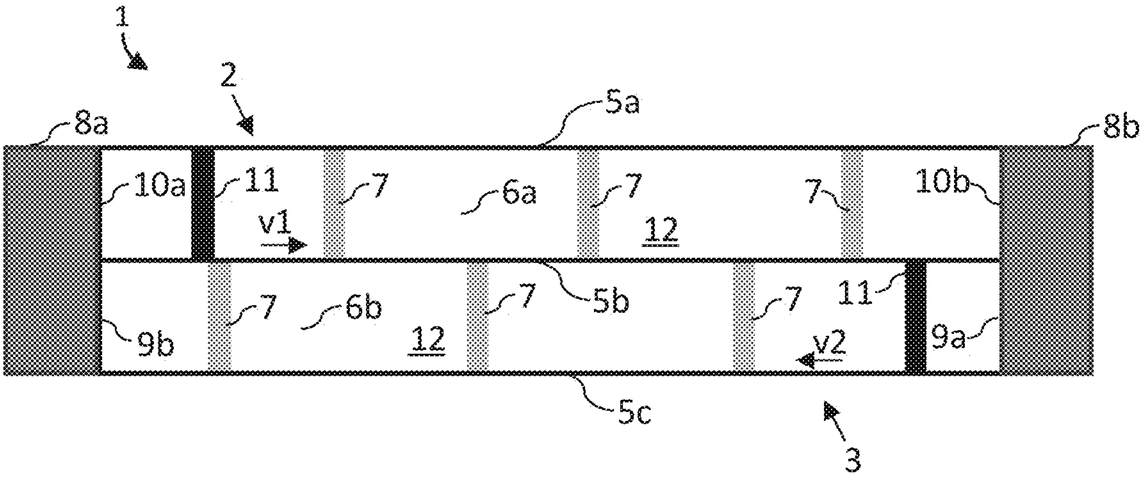
FIG. 2 is a schematic illustration of an algae cultivation system in accordance with some embodiments of the present disclosure.

II. Algae Cultivation System:

The present disclosure provides an algae cultivation system 1. FIG. 2 illustrates an algae cultivation system 1 in accordance with some embodiments of the present disclosure. The algae cultivation system 1 includes a first channel 2. The channel bottom may be flat or sloped. In some embodiments, the first channel 2 includes a sloped bottom 6*a* and opposing side walls 5*a*, 5*b* coupled to the sloped bottom 6*a*. A pump system 8*a*, 8*b* moves an algae cultivation fluid 12 from the first channel 2 to a second channel 3. The second channel 3 includes a sloped bottom 6*b* and opposing sidewalls 5*b*, 5*c* coupled to the sloped bottom 6*b*. As illustrated in FIG. 2, the channels 2, 3 may share a central sidewall 5*b*. Although not illustrated in FIG. 2, each channel 2, 3 may be separated by a spacing where each channel 2, 3 has its own opposing sidewalls.

In some embodiments, the pump 8*a* moves the algae cultivation fluid 12 within channel 2 along a flow path v1 that extends from a high end 10*a* to a low end 10*b* of the sloped bottom 6*a*. The pump 8*b* may receive the algae cultivation fluid 12 at the low end 10*b*, and move the algae cultivation fluid 12 from the low end 10*b* of sloped bottom 6*a* in the first channel 2 to a high end 9*a* of sloped bottom 6*b* in the second channel 3.

In some embodiments, the pump 8*b* moves the algae cultivation fluid 12 within channel 3 along a flow path v2 that extends from the high end 9*a* to a low end 9*b* of the sloped bottom 6*a*. In some embodiments, the pump 8*a* moves the algae cultivation fluid 12 from the low end 9*b* of sloped bottom 6*b* in the second channel 3 to a high end 10*a* of sloped bottom 6*a* in the first channel 2. In this way, the pump system 8*a*, 8*b* circulate the algae cultivation fluid 12 through the algae cultivation system 1.

Although FIG. 2 illustrates a two channel system, it is to be appreciated that a series of interconnected channels may be used. For example, rather than using pump 8*a* to recirculate the algae cultivation fluid 12 flowing from the second channel 3 to the first channel 2, a third pump (not shown) could move the algae cultivation fluid 12 from the low end 9*b* of the sloped bottom 6*b* to a high end of a sloped bottom in a third channel (not shown). This process may be repeated using a series of channels having the same or similar structure to channels 2, 3. In some embodiments, the algae cultivation system 1 includes at least 2 channels, or at least 3 channels, or at least 4 channels, or at least 5 channels, to fewer than 10 channels, or fewer than 20 channels, or fewer than 30 channels, or more. In some embodiments, a last channel in the series of channels may include a recirculation loop that is connected to the high end 10*a* of the first channel 2, establishing a continuous flow loop for the algae cultivation fluid 12 within the algae cultivation system 1. Additionally, it is to be appreciated that a single channel system may be used. For example, the pump system 8*a*, 8*b* may circulate the algae cultivation fluid 12 in a continuous loop within a single channel, which may be sloped or flat.

In some embodiments, the channels 2, 3 have a cross-sectional shape that includes, but is not limited to, a square, a rectangular, or a trapezoidal shape. In some embodiments, the channels 2, 3 have a square or rectangular cross-sectional shape where the opposing sidewalls 5*a*, 5*b*, 5*c* are perpendicular to the sloped bottom 6*a*. In some embodiments, the opposing sidewalls 5*a*, 5*b*, 5*c* may be slanted at an angle creating a trapezoidal cross-sectional shape.

In some embodiments, the channels 2, 3 are earthen channels. As used herein, the term "earthen channel" may refer to an elongate void in the earth where the sidewalls 5*a*, 5*b*, 5*c* and the sloped bottoms 6*a*, 6*b* are composed of earthen materials, such as soil. The earthen channel may be lined with a liner. Suitable liners include, but are not limited to, plastic liners and building materials, such as concrete, cement, mortar, brick, and combinations thereof.

In some embodiments, the algae cultivation system 1 includes a bore wave generator 11 positioned in the one or more channel 2, 3. The bore wave generator 11 may be positioned downstream of the pumps 8*a*, 8*b*.

Figure 3:
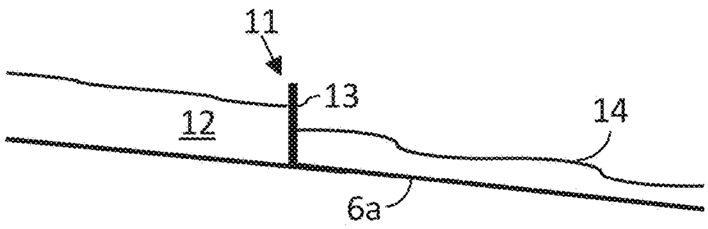
FIG. 3 is a cross-sectional view of a bore wave generator in accordance with some embodiments of the present disclosure.

Referring to FIG. 3, the bore wave generator 11 may include a moveable gate 13 that impedes or prevents the flow of algae cultivation fluid 12 within the channels 2, 3. When in a closed position, the moveable gate 13 accumulates algae cultivation fluid 12 on the pump side of the gate 13. The gate 13 may periodically displace (e.g., lift) to release a bore wave of algae cultivation fluid 12 that flows down the channels 2, 3.

In some embodiments, the gate 13 is displaced at a frequency from 10 to 300 seconds, which may be used to control a bore wave frequency within the channels 2, 3. In some embodiments, the gate 13 is displaced manually, or controlled by a controller, at a frequency of at least 10 seconds, or at least 15 seconds, or at least 30 seconds, or at least 45 seconds, or at least every 60 seconds, to fewer than 90 seconds, or fewer than 120 seconds, or fewer than 150 seconds, or fewer than 180 seconds, or fewer than 240 seconds, or fewer than 300 seconds. The bore wave frequency is increased proportionally to the flow pumps 8*a*, 8*b*, i.e. a higher flow rate is required for higher frequency and a lower flow rate for lower frequency.

In some embodiments, the flow generated by pumps 8*a*, 8*b* is increased while the displaced frequency for gate 13 is held constant to increase the intensity of the bore wave by increasing the height and volume of fluid behind the gate prior to displacing the gate. The flow generated by pumps 8*a*, 8*b* can also be decreased to lower the intensity of the bore wave. In some embodiments, the gate 13 is displaced when the height of the fluid behind the gate compared to the height of the fluid downstream of the gate is at least 2 cm or at least 4 cm or at least 6 cm or at least 10 cm or at least 20 cm or at least 30 cm to less than 60 cm or less than 90 cm or less than 120 cm. The height of fluid may be monitored or determined using a sensor (e.g., level sensor).

Figure 4:
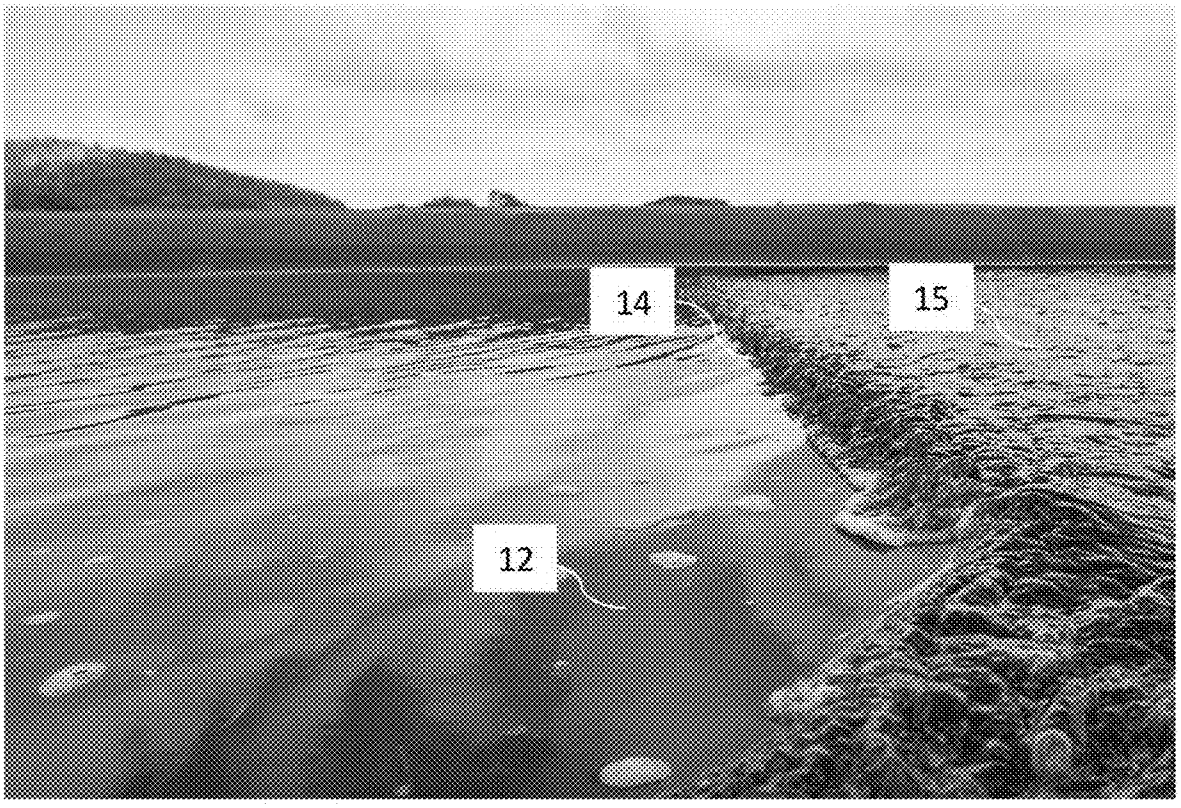
FIG. 4 is an image of an exemplary bore wave in accordance with some embodiments of the present disclosure.

Bore waves create intense mixing between air and the algae cultivation fluid 12, as illustrated in FIG. 4. The wave front 14 is constantly breaking, which creates additional surface area from the splashing and the height of the wave front 14. Further, the wave front 14 entraps air that is driven down into the algae cultivation fluid 12. As the wave front 14 passes, these air bubbles are mixed in the high turbulence that follows the wave 15 before eventually rising to the surface. This generates a large amount of additional gas-liquid interface area together with high mixing rates that reduces the boundary layer and increases carbon dioxide and nitrogen absorption rate per area. The bore wave frequency or intensity can be varied, so that higher surface area and mixing are generated, e.g. increasing the wave frequency or intensity to provide more carbon dioxide during the high productivity times, and lower energy is used during lower productivity periods, e.g. reducing the wave frequency or intensity.

Referring back to FIG. 2, in some embodiments, the algae cultivation system 1 includes at least one air-liquid mixing device 7. The at least one air-liquid mixing device 7 is configured to disrupt an air-liquid interface on the algae cultivation fluid 12 to enhance the absorption rate of atmospheric carbon dioxide and atmospheric nitrogen.

In some embodiments, the channels 2, 3 includes from 2 to 30 air-liquid mixing devices. In some embodiments, the channels 2, 3 includes at least 2 air-liquid mixing devices, or at least 3, or at least 4, or at least 5, to fewer than 10, or fewer than 15, or fewer than 20, or fewer than 25, or fewer than 30.

In some embodiments, the channels 2, 3 includes from 1 to 30 bore wave generators 11. In some embodiments, the channels 2,3 includes at least 1 bore wave generators 11, or at least 2, or at least 3, or at least 5, to less than 10, or less than 15, or less than 20, or less than 25, or less than 30.

In some embodiments, the air-liquid mixing device 7 may be powered by the flow of algae cultivation fluid 12. As used herein, the phrase "powered by the flow of algae cultivation fluid" may refer to passing the algae cultivation fluid 12 through and/or around the air-liquid mixing device 7 at a velocity sufficient to disrupt an air-liquid interface of the algae cultivation fluid to induce direct absorption of atmospheric carbon dioxide or atmospheric nitrogen into the algae cultivation fluid 12. In some embodiments, the phrase "powered by the flow of algae cultivation fluid" may refer to circulating the algae cultivation fluid 12 within the at least one channel 2, 3 at a velocity that is sufficient to move the air-liquid mixing device 7 to cause the air-liquid mixing device to disrupt an air-liquid interface of the algae cultivation fluid to induce direct absorption of atmospheric carbon dioxide or atmospheric nitrogen into the algae cultivation fluid 12.

Figure 5:
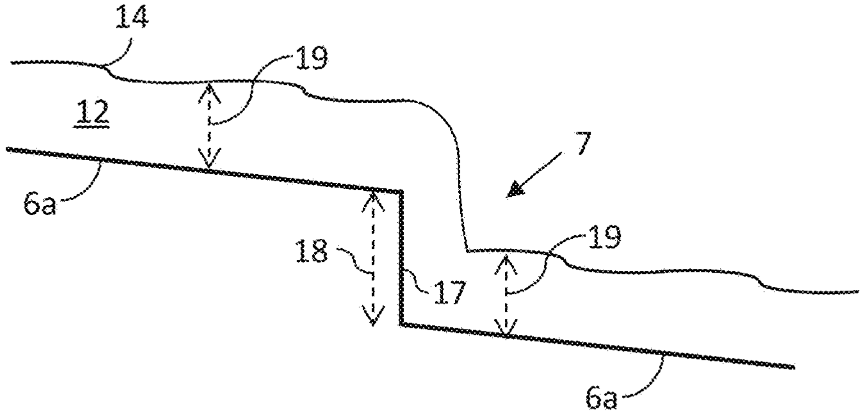
FIG. 5 is a schematic illustration of an air-liquid mixing device in accordance with some embodiments of the present disclosure.

FIG. 5 illustrates a cross-sectional view of an exemplary air-liquid mixing device 7 positioned in channel 2 of FIG. 2. In some embodiments, the air-liquid mixing device 7 includes a drop-off 17 (e.g., higher sloped region or vertical drop off region) in the sloped bottom 6*a*. The drop-off 17 generates a high mixing rate that enhances the gas-liquid interface area, and increases the carbon dioxide and/or nitrogen absorption rate into the algae cultivation fluid 12.

In some embodiments, a height 18 of the drop-off 17 is greater than a depth 19 of the algae cultivation fluid 12 within the channel 2. In some embodiments, the depth 19 of the algae cultivation fluid 12 is defined by a distance between an air-liquid interface of the algae cultivation media to the sloped bottom 6*a*.

In some embodiments the height 18 of the drop-off 17 is at least 1.1 times greater than the depth 19 of the algae cultivation fluid 12, or at least 1.2 times greater, or at least 1.3 times greater, or at least 1.4 times greater, or at least 1.5 times greater, or at least 1.6 times greater, or at least 1.7 times greater, or at least 1.8 times greater, or at least 1.9 times greater, to less than 2 times greater, or less than 2.5 times greater, or less than 3 times greater, or less than 3.5 times greater, or less than 4 times greater, or less than 5 times greater, or less than 6 times greater, or less than 7 times greater, or less than 8 times greater, or less than 9 times greater, or to less than 10 times greater.

In some embodiments, the height 18 of the drop-off 17 is at least 1 centimeter (cm) greater than the depth 19 of the algae cultivation fluid 12. In some embodiments, the height 18 of the drop-off 17 is at least 1 cm greater than the depth 19, or at least 2 cm, or at least 3 cm, or at least 4 cm, or at least 5 cm, or at least 6 cm, or at least 7 cm, or at least 8 cm, or at least 9 cm, or at least 10 cm, or at least 11 cm, or at least 12 cm, or at least 13 cm, or at least 14 cm, or at least 15 cm, to less than 20 cm, or less than 25 cm, or less than 30 cm, or less than 40, or less than 50, or less than 100 cm.

In some embodiments, the depth 19 of the algae cultivation fluid 12 is at least 1 cm, or at least 2 cm, or at least 3 cm, or at least 4 cm, or at least 5 cm, or at least 6 cm, or at least 7 cm, or at least 8 cm, or at least 9 cm, or at least 10 cm, to less than 15 cm, or less than 20 cm, or less than 30 cm, or less than 40 cm, or less than 50 cm.

In some embodiments, the drop-off 17 has a slope percentage that is greater than a slope percentage of the sloped bottom 6*a*. In some embodiments, the sloped bottom 6*a* continues after the drop-off 17 with the same or different slope percentage than the sloped bottom 6*a* upstream of the drop-off 17.

In some embodiments, the sloped bottoms 6*a*, 6*b* have a slope percentage of at least 0.1%. In some embodiments, the sloped bottoms 6*a*, 6*b* have a slope percentage of at least 0.01%, or at least 0.02%, or at least 0.03%, or at least 0.04%, or at least 0.05%, to less than 0.06%, or less than 0.07%, or less than 0.08%, or less than 0.09%, or less than 0.1%, or less than 0.5%, or less than 1%, or less than 2%, or to less than 3%. As used herein, the term "slope percentage" may refer to the slope of the sloped bottoms 6*a*, 6*b* expressed as a percentage, e.g., (rise length/run length)×100.

In some embodiments, the drop-off 17 has a steep slope percentage of at least 100%, or at least 200%, or at least 300%, or at least 400%, or at least 500%, or at least 600%, to less than 700%, or less than 800%, or less than 900%, or less than 1000%, or to a vertical drop-off.

Figure 6:
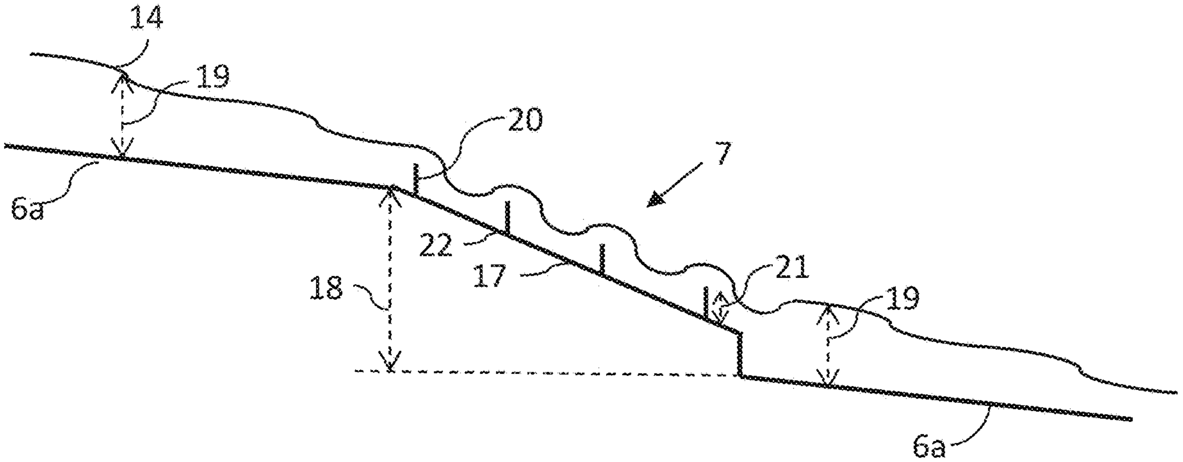
FIG. 6 is a schematic illustration of an air-liquid mixing device in accordance with some embodiments of the present disclosure.

As shown in FIG. 6, the drop-off 17 may include one or more weir 20. As used herein, the term "weir" may refer to a barrier across at least a portion of the width of the channel that alters the flow characteristics of the algae cultivation fluid 12. Passing the algae cultivation fluid 12 over the weirs creates turbulence and high air-liquid mixing rates, thereby enhancing the absorption rate of carbon dioxide and/or nitrogen into the algae cultivation fluid 12.

In some embodiments, a height 21 of the weir 20 is less than the depth of the algae cultivation fluid 12 so that the fluid flows over the top of the weir 20. In some embodiments, the height 21 of the weir 20 extends at least 50% of a depth of the algae cultivation fluid 12 above the drop-off 17, or at least 55%, or at least 60%, or at least 65%, or at least 70%, or at least 75%, to less than 80%, or less than 85%, or less than 90%, or less than 95% of the depth.

In some embodiments, the one or more weir 20 extends at least 10% the width of the channels 2, 3. In some embodiments, the one or more weir 20 extends at least 10% the width of the channels 2, 3, or at least 20%, or at least 30%, or at least 40%, or at least 50%, or at least 60%, or at least 70%, to less than 80%, or less than 90%, or the less than 95%, or to the entire width of the channels 2, 3.

In some embodiments, the drop-off 17 includes a series of weirs 20 along the length of the drop-off 17. In some embodiments, the drop-off 17 includes from 1 to 50 weirs 20. In some embodiments, the drop-off 17 includes at least 2 weirs, or at least 3 weirs, or at least 4 weirs, or at least 5 weirs, or at least 6 weirs, or at least 7 weirs, or at least 8 weirs, or at least 9 weirs, to fewer than 10 weirs, fewer than 20 weirs, fewer than 30 weirs, fewer than 40 weirs, or fewer than 50 weirs.

In some embodiments, the drop-off 17 has a low slope percentage of at least 0.3%, or at least 0.4%, or at least 0.5%, or at least 0.6%, or at least 0.7%, or at least 0.8%, or at least 0.9%, or at least 1%, or at least 1.5%, or at least 2%, or at least 2.5%, or at least 3%, or at least 3.5%, or at least 4%, or at least 4.5%, to less than 5%, or less than 6%, or less than 7%, or less than 8%, or less than 9%, or less than 10%.

In some embodiments, the one or more weir 20 includes a passage 22 that allows algae cultivation fluid 12 to drain. The passage 22 may allow the algae cultivation fluid 12 to flow through or around the one or more weir 20. In some embodiments, the passage 22 is a hole located in the bottom of the one or more weir 20. The passage 22 may be sized such that algae cultivation fluid 12 can drain from the drop-off 17 when recirculation ceases, but is small enough such that a majority of the algae cultivation fluid flows over the one or more weir 20 during operation. In some embodiments, the weir 20 may have a notch in the plate that has a geometric shape. The notch in the weir 20 may have a triangular (v-shaped), rectangular, trapezoidal, or a compound shape (having at least two notch shapes in the weir).

Figure 7:
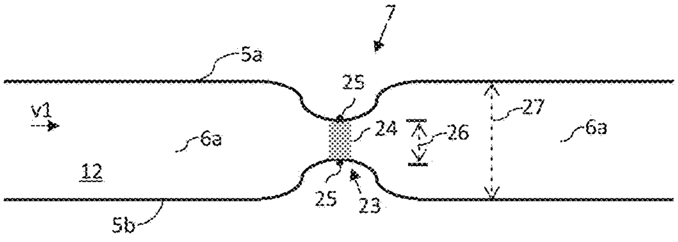
FIG. 7 is a schematic illustration of an air-liquid mixing device in accordance with some embodiments of the present disclosure.

FIG. 7 illustrate a top and side view of an exemplary air-liquid mixing device 7 positioned in channel 2 of FIG. 2. The air-liquid mixing device 7 includes a narrowed region 23 having a reduced cross-sectional area relative to the channel 2. In some embodiments, the narrowed region 23 is formed from the opposing sidewalls 5*a*, 5*b* protruding inward to form a reduced cross-sectional area with increased fluid velocity. The narrowed region 23 includes a diffuser 24 and one or more pipe 25 that rises above the surface of the algae cultivation fluid 12 to place the diffuser 24 in fluid communication with the atmosphere.

The increased fluid velocity within the narrowed region 23 utilizes the Bernoulli effect to pull air from the atmosphere to the diffuser 24. The diffuser 24 includes a series of apertures that dispense the air into the algae cultivation fluid 12 (e.g., as bubbles). The bubbles have a high surface area and increase the absorption of carbon dioxide and/or nitrogen into the algae cultivation fluid 12.

In some embodiments, the sidewalls 5*a*, 5*b* within the narrowed region 23 may have a geometric shape. In some embodiments, the geometric shape of the sidewalls 5*a*, 5*b* in the narrowed region 23 include, but is not limited to, an arcuate shape, a slanted shape, a square or rectangular shape. Alternatively or additionally, the narrowed region 23 may be formed by adding a building material to the channel 2, such as soil, concrete, mortar, cement, and combinations thereof, to reduce the cross section of the channel 2.

In some embodiments, the narrowed region 23 has a width 26. In some embodiments, the width 26 of the narrowed region 23 is less than 95% of a width 25 of the channel 2, or less than 90%, or less than 85%, or less than 80%, or less than 70%, or less than 60%, or less than 50%, or less than 40%, to at least 30%, or at least 20%, or at least 10% of the width 27 of the channel 2.

Figure 8:
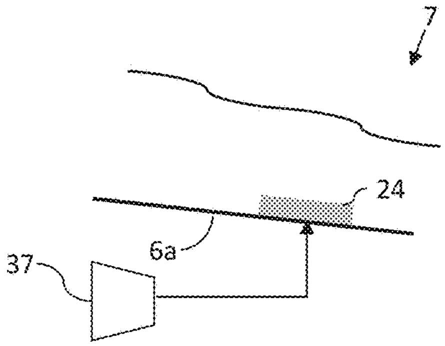
FIG. 8 is a schematic illustration of an air-liquid mixing device in accordance with some embodiments of the present disclosure.

FIG. 8 provides a side view of an exemplary air-liquid mixing device 7 which includes an air transfer device 37 (e.g., blower or compressor) that is coupled to a diffuser 24 to generate bubbles in the algae cultivation fluid 12. The bubbles can be generated in a higher velocity zone or a zone with static mixers to provide additional turbulence to reduce the boundary layers and provide greater $CO_2$ and/or $N_2$ absorption rate per gas-liquid area generated. Also, the size of the bubbles created can be controlled to provide enough residence time in the media for absorption of $CO_2$ and/or $N_2$ from the air bubble. The size of the bubbles can be optimized based on pH, molarity, and cost of generating the bubbles versus $CO_2$ capture efficiency to minimize the effective cost of $CO_2$ supplied from the air. The blower or compression devices can be powered by the flow of media including the flow of a bore wave. Advantages of using the flow of the media and/or flow of bore waves to power a device is that the expense of installing and maintaining power wiring is avoided, and for bore waves, mixing can be varied based on the frequency and/or intensity of the waves.

In some embodiments, the bubbles can be generated by the air transfer device at a higher rate when each bore wave passes by so the bubbles will be entrained longer with more vigorous local mixing to increase the max transfer efficiency. Timing the release of bubbles in this way results in more efficient use of the energy used to generate bubbles because they are added when the efficiency of $CO_2$ and/or $N_2$ transfer is highest.

In some embodiments, the diffuser 24 extends along at least a portion or the entire width 26 of the narrowed region 23. In some embodiments, a series of pipes 25 are used to provide air to the diffuser. In some embodiments, from two to ten pipes 25 are used. In some embodiments, the one or more pipes 25 are positioned proximate or in contact with the sidewalls 5*a*, 5*b* of the narrowed region 23.

Figure 9:
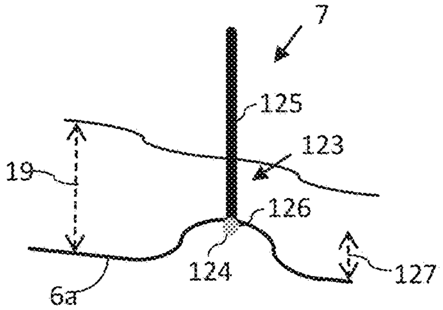
FIG. 9 is a schematic illustration of an air-liquid mixing device in accordance with some embodiments of the present disclosure.

FIG. 9 illustrates a side view of an exemplary air-liquid mixing device 7 positioned in channel 2 of FIG. 2. The air-liquid mixing device 7 includes a narrowed region 123 having a reduced cross-sectional area relative to the channel 2. In some embodiments, the narrowed region 123 is formed from the sloped bottom 6*a* generating a protrusion 126 that extends vertically upwards to reduce the depth 19 of the algae cultivation fluid in the narrowed region 123 to form a reduced cross-sectional area with increased fluid velocity.

The narrowed region 123 includes a diffuser 124 and one or more pipe 125 that rises above the surface of the algae cultivation fluid 12 to place the diffuser 124 in fluid communication with the atmosphere. The diffuser 124 includes a series of apertures that dispense the air into the algae cultivation fluid 12. The diffuser 124 is placed in the narrowed region 123 where the increased fluid velocity produces a low enough pressure via the Bernoulli effect to pull air into the algae cultivation fluid 12 through the one or more pipes 125 and the diffuser 124.

In some embodiments, the protrusion 126 in the sloped bottom 6*a* has a geometric shape. In some embodiments, the geometric shape of the protrusion 26 in the narrowed region 23 includes, but is not limited to, arcuate walls forming a hemispherical shape, a slanted shape forming a triangular or trapezoidal shape, or vertical walls forming a square or rectangular shape.

In some embodiments, the protrusion 126 has a height 127 that is at least 5% of the depth 19 of the algae cultivation fluid (e.g., measured as the distance from the air-liquid interface to the sloped bottom 6*a*), or at least 10%, or at least 15%, or at least 20%, or at least 25%, or at least 30%, or at least 35%, or at least 40%, or at least 45%, to less than 50%, or less than 55%, or less than 60%, or less than 65%, or less than 70%, or less than 75%, or less than 80%, or less than 85%, or less than 90%, or less than 95% of the depth 19.

In some embodiments, the diffuser 124 extends along at least a portion or the entire width of the narrowed region 123. In some embodiments, a series of pipes 125 are used to provide air to the diffuser 124. In some embodiments, from 2 to 10 pipes 25 are used. In some embodiments, the one or more pipes 125 are positioned proximate or in contact with the sidewalls 5*a*, 5*b* of the narrowed region 123.

Figure 10:
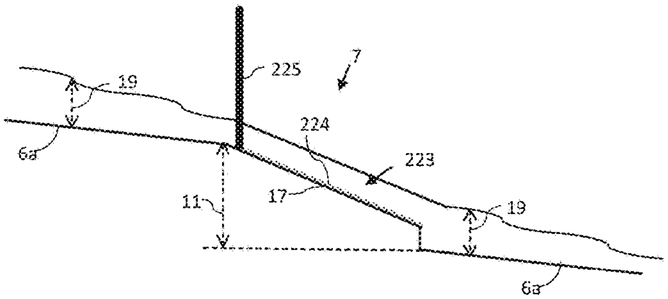
FIG. 10 is a schematic illustration of an air-liquid mixing device in accordance with some embodiments of the present disclosure.

FIG. 10 illustrates a side view of an example air-liquid mixing device 7 positioned in channel 2 of FIG. 2. As shown in FIG. 10, the diffuser 224 and one or more pipe 225 may be configured on a drop-off 17, which may produce a narrowed region 223 having a reduced cross sectional area. In some embodiments, the diffuser 224 extends along at least a portion or the entire length of the drop-off 17. In some embodiments, the diffuser 224 extends along at least 10% of the length of the drop-off 17, or at least 20%, or at least 30%, or at least 40%, or at least 50%, or at least 60%, or at least 70%, or at least 80%, or at least 90%, or 100% of the length of the drop-off 17.

Figure 11:
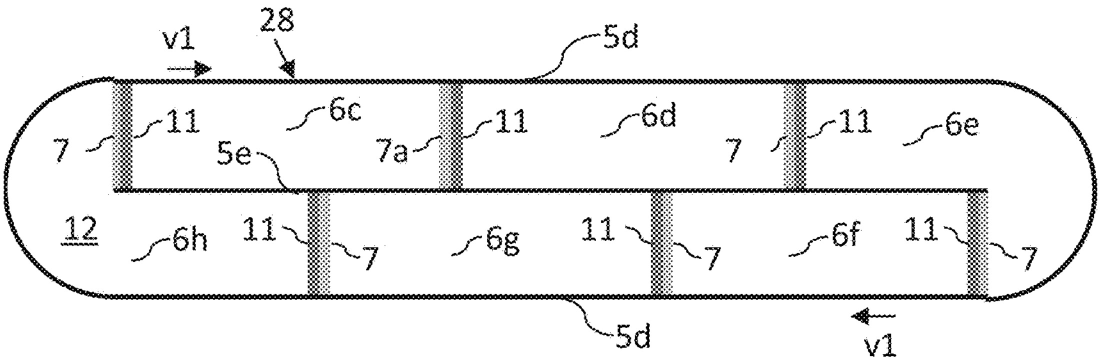
FIG. 11 is a schematic illustration of an algae cultivation system in accordance with some embodiments of the present disclosure.

FIG. 11 illustrates an algae cultivation system 1 in accordance with some embodiments of the present disclosure. The algae cultivation system 1 includes a channel 28 having sloped bottoms 6(*c-h*), an outer sidewall 5*d*, and an inner sidewall 5*e* coupled to the sloped bottoms 6(*c-h*). In some embodiments, the outer sidewall 5*d* forms an elliptical shape and the inner side wall 5*e* is disposed within the outer sidewall 5*d* (e.g., centrally disposed) to form a continuously looping channel 28.

In some embodiments, the algae cultivation system 1 includes from 2 to 30 air-liquid mixing devices 7 positioned within the channels 2, 3. In some embodiments, the channel 28 includes at least 2 air-liquid mixing devices 7, or at least 3, or at least 4, or at least 5, to less than 10, or less than 15, or less than 20, or less than 25, or less than 30.

In some embodiments, the algae cultivation system 1 includes one or more bore wave generator 11 and one or more air-liquid mixing device 7 disposed within the channel 28. In some embodiments, the algae cultivation system 1 includes a series of sloped bottoms 6(*c-h*), each of which extends from a high end to a low end. In some embodiments, the wave generators 11 and the air-liquid mixing devices 7 segment the channel 28 into the sloped bottom 6(*c-h*) regions.

Figure 12:
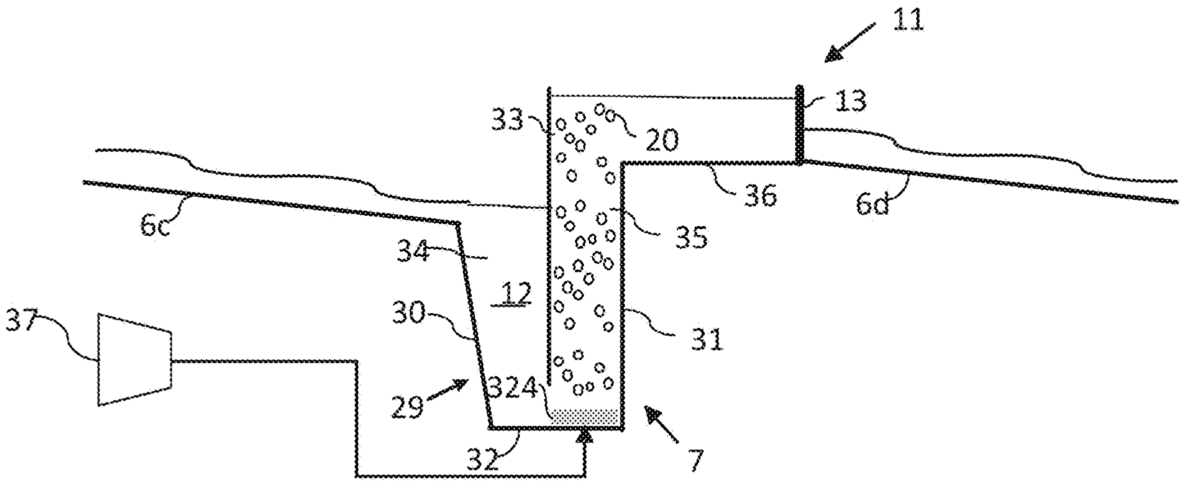
FIG. 12 is a schematic illustration of an air-liquid mixing device and bore wave generator in accordance with some embodiments of the present disclosure.

FIG. 12 illustrates an exemplary air-liquid mixing device 7 and bore wave generator 11 positioned in channel 28 of FIG. 11. In some embodiments, the sloped bottom 6*c* has a low end connected to a sump 29. The sump 29 includes opposing sump walls 30, 31 that are connected to a sump bottom 32, which may be a sloped, curved or flat. The sump 29 may include a dividing wall 33 that separates the sump 29 into a fluid collection side 34 and an air-lift side 35. In some embodiments, the air-lift side 35 includes the air-liquid mixing device 7 that transfers the algae cultivation fluid 12 from the sump 29 to a holding section 36.

In some embodiments, the air-liquid mixing device 7 includes an air transfer device 37 (e.g., blower or compressor) that is coupled to a diffuser 324 positioned on the air-lift side 35. The air transfer device 37 and diffuser 324 generate bubbles in the algae cultivation fluid 12. The bubbles lower the average density on one side of the sump 29 causing the culture media 2 to flow up that side and into the holding section 36. The flow is increased or decreased by increasing or decreasing the flow of air to the diffuser 324. The fluid within the holding section 36 is regulated using a gate 13 of a bore wave generator 11 and the rate of air flow to the diffuser 324. The gate 13 displaces at a frequency to release and generate bore waves in the channel 28. At higher frequency and the constant intensity, a greater flowrate of air to the diffuser 324 is required, and at lower frequency and constant intensity, a lower flowrate of air to the diffuser 324 is required.

In some embodiments, the channel 28 includes a pump system 8 to facilitate the flow of algae cultivation fluid 12 in the channel 28.

In some embodiments, the channel 28 includes from 2 to 30 air-liquid mixing devices 7. In some embodiments, the channel 28 includes at least 2 air-liquid mixing devices 7, or at least 3, or at least 4, or at least 5, to fewer than 10, or fewer than 15, or fewer than 20, or fewer than 25, or fewer than 30. In some embodiments, the channel 28 includes from 2 to 30 bore wave generators 11. In some embodiments, the channel 28 includes at least 2 bore wave generators 11, or at least 3, or at least 4, or at least 5, to less than 10, or less than 15, or less than 20, or less than 25, or less than 30.

In some embodiments, the channel 28 includes at least one air-liquid mixing device 7 per 300 $ft^2$ surface area of the channel 28 to one air-liquid mixing device 7 per 400,000 $ft^2$ surface area of the channel 28. In some embodiments, the channel 28 includes at least one air-liquid mixing device 7 per 400 $ft^2$ surface area of the channel 28, or at least 500 $ft^2$, or at least 1000 $ft^2$, or at least 1500 $ft^2$, or at least 2000 $ft^2$, or at least 2500 $ft^2$, or at least 3000 $ft^2$, or at least 3500 $ft^2$, or at least 4000 $ft^2$, or at least 4500 $ft^2$, or at least 5000 $ft^2$, or at least 10,000 $ft^2$, or at least 20,000 $ft^2$, or at least 30,000 $ft^2$, or at least 40,000 $ft^2$, or at least 50,0000 $ft^2$, to less than 100,000 $ft^2$, or less than 200,000 $ft^2$, or less than 300,000 $ft^2$, or less than 400,000 $ft^2$.

In some embodiments, the one or more air-liquid mixing device 7 in FIG. 2 or FIG. 11 may include fixed or rotating surfaces that break, chop or blend the surface to create splashing or bubble entrainment together with turbulent mixing. Examples of such rotating devices include disk aerators such as described in U.S. Pat. No. 4,372,895 or 9,073,016; brush aerators such as described in U.S. Pat. No. 3,561,738 or 2,684,941; paddlewheels such as described in U.S. Pat. No. 6,994,329 or 5,116,501; and surface aerators such as described in U.S. Pat. No. 6,715,912 or 6,877,959. Fixed or rotating surfaces can be combined with bore waves, cascades and/or waterfalls, for example, a waterfall could hit splash plates prior to falling into the culture media. The rotating devices could be powered by the flow of media including the flow of a bore wave. Advantages of using the flow of the media and/or flow of bore waves to power a device is that the expense of installing and maintaining power wiring is avoided, and for bore waves, mixing can be varied based on the frequency of the waves.

For devices that utilize external power such as rotating surfaces, blowers, compressors, or pumps for venturis, the rate of air-liquid surface area generation and mixing can be varied so that higher surface area and mixing are generated when it is needed to provide more $CO_2$ and/or $N_2$ during the high productivity times, and lower energy is used during lower productivity periods when it is not needed as described above for bore wave frequency. Additionally, the devices can utilize solar power to eliminate the expense of installing and maintaining power wiring throughout a multi-acre algae farm. The solar power can also be directly utilized to provide variable mixing and minimize or eliminate the battery storage requirements as described above for directly powering the wave generator.

Figure 13:
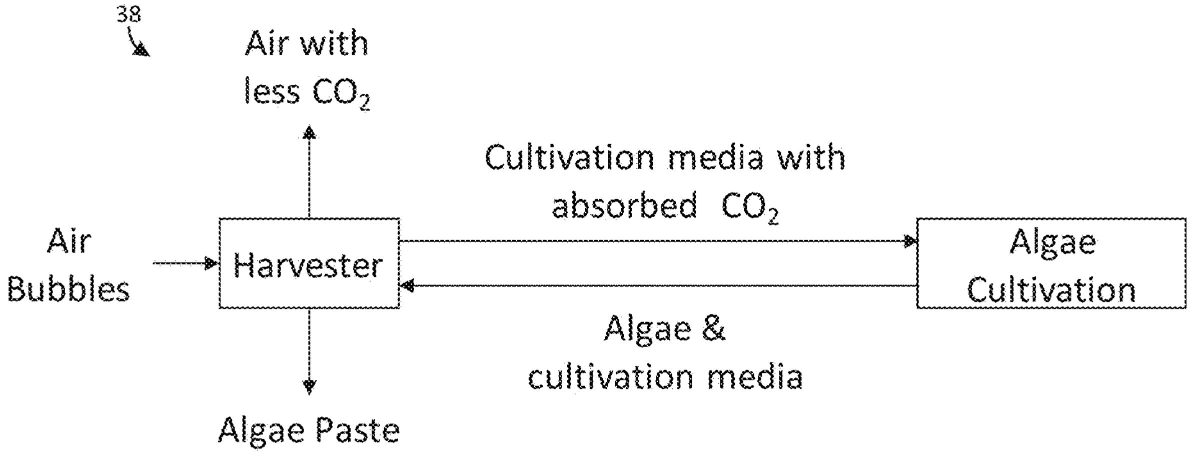
FIG. 13 is schematic illustration of an example harvester in accordance with some embodiments of the present disclosure.

FIG. 13 illustrates a system 38 for absorbing $CO_2$ from the air during harvest to provide another source of $CO_2$ that can be used for control during cultivation to improve stability and productivity in addition to the variable mixing described above. High productivity algae cultivation in large raceways with $CO_2$ supplied by direct air capture is supplemented through harvesting the algae and culture media at a high enough pH to provide a driving force for $CO_2$ capture from the atmosphere and a high enough carbonate concentration to store $CO_2$ in the media, separating the algae from the media in a harvest system that utilizes air bubbles to assist in the harvesting, absorbing $CO_2$ from the air into the media during the harvesting, and controlling return of the media containing the absorbed $CO_2$ to the cultivation system. The timing of the media return to the cultivation system can be controlled based on the weather and productivity to provide extra $CO_2$ when it is needed for pH control or to support growth.

As shown in FIG. 13, algae and algae cultivation fluid 12 are transported from the algae cultivation system 1 to a harvester, which may be done via a pump. In some embodiments, the harvester includes a housing having a liquid inlet, a retentate outlet, a permeate outlet, a gas inlet, and a gas outlet. The housing may include a membrane that separates the housing into a permeate side and a retentate side. The membrane separates the algae cultivation fluid 12 into an algae paste that exits the housing through the retentate outlet and a permeate fluid that exits the housing through the permeate outlet. The permeate containing purified algae cultivation fluid may be recycled back to the algae cultivation system 1.

In some embodiments, air is supplied to the harvester (e.g., in the form of bubbles) via a gas conduit during separation. The harvester may have a gas outlet to dispense the air having reduced carbon dioxide and/or nitrogen concentration. The permeate containing purified algae cultivation fluid 12 may be enriched in carbon dioxide and/or nitrogen as it is recycled back to the algae cultivation system 1.

The optimum pH and equivalent bicarbonate molarity for use in the algae cultivation system 1 is dependent on the species, the productivity, and contamination control. High pH and higher equivalent bicarbonate molarity can be used to limit the number of species that can contaminate a raceway. Higher equivalent bicarbonate molarity adds buffering capacity to reduce fluctuation in pH and to allow more capture and storage of $CO_2$ when the algae is not growing as fast or during harvesting. Lower equivalent bicarbonate molarity allows $CO_2$ absorption at lower pH, which accommodates more species. Each species and strain has an optimal pH and equivalent bicarbonate molarity range, and each has a different resistance to contamination. The rate of transfer across the gas-liquid interface is dependent on the pH and equivalent bicarbonate molarity. Thus, for each target species, strain, and cultivation system, there can be a separate optimal pH and equivalent bicarbonate set point.

In some embodiments, the algae cultivation system 1 includes one or more channels 2, 3, 28 having a total surface area of at least 100 square ft ($ft^2$). In some embodiments, the algae cultivation system 1 includes one or more channels 2, 3, 28 having a total surface area of at least 100 $ft^2$, or at least 200 $ft^2$, or at least 500 $ft^2$, or at least 1000 $ft^2$, or at least 5000 $ft^2$, or at least 7500 $ft^2$, or at least 10,000 $ft^2$, or at least 20,000 $ft^2$, or at least 30,000 $ft^2$, or at least 40,000 $ft^2$, or at least 50,000 $ft^2$, or at least 100,000 $ft^2$, or at least 500,000 $ft^2$ to less than 600,000 $ft^2$, or less than 1,000,000 $ft^2$, or less than 5,000,000 $ft^2$, or less than 10,000,000 $ft^2$, or less than 20,000,000 $ft^2$.

Figure 14:
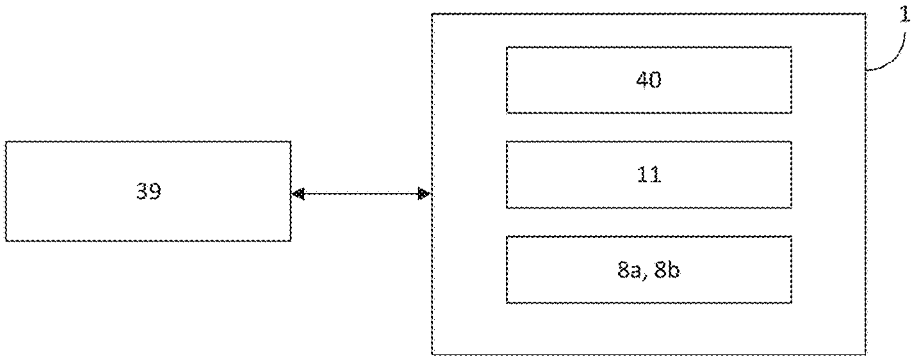
FIG. 14 is a schematic illustration of a process control system in accordance with some embodiments of the present disclosure.

II. Process Control:

Referring to FIG. 14, in some embodiments, the algae cultivation system 1 is used in conjunction with a controller 39 and one or more process measuring devices 40 configured to monitor a process parameter (e.g., pH, dissolved oxygen content, atmospheric light intensity, nitrogen concentration, carbon dioxide concentration, turbidity, optical density, and biomass productivity, algae cultivation fluid height) in the algae cultivation system 1 and/or the algae cultivation fluid 12. In some embodiments, the process measuring devices 40 include one or more sensors configured in the algae cultivation system 1 or in the algae cultivation fluid 12. Non-limiting examples of suitable sensors include pH sensors, a dissolved oxygen level sensor, a light intensity sensor, a level sensor, or combinations thereof. The pH sensor may be configured to monitor the pH of the algae cultivation fluid.

The controller 39, the one or more process measuring devices 40, the bore wave generator 11, the pump system **8*a*, 8*b*, and optionally an air blower or valve in the diffusers 24 or air mixing devices 7 may be placed in electrical communication to send and receive electrical signals. Suitable connections may include transmitters that allow process signals, such as electrical signals, to be transmitted between the controller 39, the measuring devices 40, and the bore wave generator 11**.

In some embodiments, the electrical signals may be transferred via a wired connection or through a wireless network connection. Other hardware elements may be included in the process control system, for example, transducers, analog-to-digital (A/D) converters, and digital-to-analog (D/A) converters that allow process information to be recognizable in computer form, and computer commands accessible to the process.

The controller 39 includes a processor and a memory that includes software and data, and is designed for storage and retrieval of processed information to be processed by the processor. The processor may receive input data or process signals from the measuring devices 40 and the bore wave generator 11. The controller 39 may operate autonomously or semi-autonomously, or may read executable software instructions from the memory or a computer-readable medium (e.g., a hard drive, a CD-ROM, flash memory), or may receive instructions via the input from a user, or another source logically connected to a computer or device, such as another networked computer or server. For example, the server may be used to control the bore wave generator 11 via the controller 39 on-site or remotely.

The processor may process the process the signals to generate an output, which may take the form of a process control action. Example process control actions may include adjusting the bore wave frequency in the channels 2, 3, 28 using the bore wave generator 11 in response to measured values obtained from the one or more measuring devices 40. The bore wave frequency, intensity or a combination thereof may be adjusted to alter and/or maintain a desired set point of one or more process parameter (e.g., maintain a desired pH, carbon dioxide concentration, nitrogen concentration, dissolved oxygen content).

In some embodiments, the bore wave frequency, bore wave intensity, and/or air mixing device intensity can be varied, so that higher or lower surface area and mixing are generated, e.g. increasing the wave frequency to provide more carbon dioxide during the high productivity times and reducing the wave frequency during lower productivity periods.

During high productivity, the algae utilize carbon dioxide at a sufficient rate such that the relative carbonate-bicarbonate-dissolved carbon dioxide concentrations in the algae cultivation fluid are not in equilibrium and the partial pressure of carbon dioxide from the media is lower than in equilibrium. In these high productivity periods, the driving force for carbon dioxide absorption is greater than predicted from equilibrium calculations. Also, in these periods, carbon dioxide can be absorbed from the air at a pH lower than the equilibrium pH. The effect of increasing wave frequency during higher productivity periods is magnified because much larger gas-liquid area and mixing are generated at the same time as a higher driving force is available for $CO_2$ absorption. Varying the wave frequency thus increases the absorption rate with a lower total energy use.

The pH of the media is increased by algae growth as $CO_2$ is removed from the media. The pH is decreased as $CO_2$ is absorbed from the atmosphere. Since the wave frequency provides a mechanism to control the absorption rate, the wave frequency can be used to maintain a specific pH during cultivation.

Nitrogen fixing algae remove dissolved nitrogen from the cultivation media creating a driving force for absorption of nitrogen from the air. Unlike carbon dioxide which can be stored within the algae cultivation fluid as bicarbonate for later use, nitrogen is only stored in a limited quantity as a dissolved gas. Typically, the stored quantity of dissolved nitrogen is not sufficient to supply the nitrogen needed for high productivity. Therefore, higher absorption rate is required to support growth during high productivity periods. By varying the wave frequency and/or air flow to the diffusers 24 to generate higher surface area and mixing during periods of higher productivity, sufficient $N_2$ can be provided to support growth of nitrogen-fixing algae.

An example method for varying the wave frequency or intensity is to utilize solar energy directly to provide power for the pump for wave generation. This will automatically increase the wave frequency or intensity during higher light intensity-higher productivity periods and reduce it during lower light intensity-lower productivity periods. Furthermore, it will reduce the cost of using solar energy to supply energy for the wave generator because the need for battery storage is greatly reduced compared to operating at a constant wave frequency. A small portion of the solar energy could be stored to provide a minimum level of mixing during very low light intensity or at night.

In some embodiments, the controller 39 adjusts the bore wave generator 11 to release bore waves within the channels 2, 3, 28 at a wave frequency. In some embodiments, the frequency is adjusted by lifting the gate 13 of the bore wave generator 11 at least every 10 seconds, or at least 15 seconds, or at least 30 seconds, or at least 45 seconds, or at least every 60 seconds, to less 90 seconds, or less than 120 seconds, or less than 150 seconds, or less than 180 seconds, or less than 240 seconds, or less than 300 seconds. The gate displacement rate may be used to control the bore wave frequency within the channels 2, 3, 28.

In some embodiments, the wave frequency, intensity or a combination thereof is adjusted using the bore wave generator 11 to maintain a desired pH of the algae cultivation fluid 12. In some embodiments, the one or more measuring device 40 is a pH sensor that monitors the pH of the algae cultivation fluid 12. In some embodiments, the wave frequency, intensity or a combination thereof is adjusted to maintain a desired pH of at least 9.5, or at least 9.8, or at least 9.9, or at least 10, or at least 10.1, or at least 10.2, or at least 10.3, or at least 10.4, to less than 10.5, or less than 10.6, or less than 10.7, or less than 10.8, or less than 10.9, or less than 11.

In some embodiments, the wave frequency, intensity or a combination thereof is adjusted using the bore wave generator 11 to maintain a desired dissolved oxygen content. In some embodiments, the one or more measuring device 40 is a dissolved oxygen content sensor that monitors the dissolved oxygen content of the algae cultivation fluid 12. In some embodiments, the wave frequency, intensity or a combination thereof is adjusted to maintain a desired dissolved oxygen content of at least 100% oxygen saturation, or at least 120%, or at least 140%, or at least 160%, or at least 180% to less than 200%, or less than 300%, or less than 400%, or less than 500% oxygen saturation.

In some embodiments, the wave frequency, intensity or a combination thereof is adjusted using the bore wave generator 11 to disrupt an air-liquid interface of the algae cultivation fluid 12 to induce direct absorption of atmospheric carbon dioxide from air into the algae cultivation fluid 12 such that a majority of the carbon in the algae and/or carbon dioxide dissolved in the algae cultivation fluid 12 is from the atmospheric carbon dioxide, or at least 55% is from atmospheric carbon dioxide, or at least 60%, or at least 65%, or at least 70%, or at least 75%, or at least 80%, or at least 85%, to less than 90%, or less than 95%, or 100% of the carbon dioxide is from atmospheric carbon dioxide.

In some embodiments, the carbon content in the algae or the carbon dioxide content in the algae cultivation fluid 12 may be measured using methods known to the skilled artisan, such as a CHN analyzer or a gas sensing electrode (e.g., carbon dioxide sensing electrode). In some embodiments, isotropic analysis may be used to carbon date the carbon in the algae or carbon dioxide in the algae cultivation fluid 12. This may be used to estimate how much carbon in the algae or carbon dioxide dissolved in the algae cultivation fluid 12 is derived from atmospheric carbon dioxide versus other carbon sources (e.g., flue gas). For example, flue gas typically has an older carbon date relative to carbon dioxide derived from the atmosphere.

In some embodiments, the wave frequency, intensity or a combination thereof is adjusted using the bore wave generator 11 to maintain a minimum bicarbonate concentration obtained through the absorption of atmospheric carbon dioxide. In some embodiments, the wave frequency, intensity or a combination thereof is adjusted to maintain a minimum bicarbonate concentration of at least 1 mM throughout the entire volume of the algae cultivation fluid 12, or at least 5 mM, or at least 10 mM, or at least 15 mM, or at least 20 mM, or at least 25 mM, or at least 30 mM, or at least 35 mM, or at least 40 mM, or at least 45 mM, or at least 50 mM, or at least 60 mM, or at least 70 mM, or at least 80 mM, or at least 90 mM, to less than 100 mM, or less than 110 mM, or less than 120 mM, or less than 130 mM, or less than 140 mM, or less than 150 mM, or less than 160 mM, or less than 170 mM, or less than 180 mM, or less than 190 mM, or less than 200 mM, or less than 300 mM, or less than 400 mM, or less than 500 mM.

In some embodiments, the wave frequency, intensity or a combination thereof is adjusted using the bore wave generator 11 to maintain an average equivalent bicarbonate concentration obtained through the absorption of atmospheric carbon dioxide. In some embodiments, the wave frequency, intensity or a combination thereof is adjusted to maintain an average equivalent bicarbonate concentration of sodium ions of at least 1 mM throughout the entire volume of the algae cultivation fluid 12, or at least 5 mM, or at least 10 mM, or at least 15 mM, or at least 20 mM, or at least 25 mM, or at least 30 mM, or at least 35 mM, or at least 40 mM, or at least 45 mM, or at least 50 mM, or at least 60 mM, or at least 70 mM, or at least 80 mM, or at least 90 mM, to less than 100 mM, or less than 110 mM, or less than 120 mM, or less than 130 mM, or less than 140 mM, or less than 150 mM, or less than 160 mM, or less than 170 mM, or less than 180 mM, or less than 190 mM, or less than 200 mM, or less than 300 mM, or less than 400 mM, or less than 500 mM.

In some embodiments, an equivalent bicarbonate concentration of sodium ions in the algae cultivation fluid and the bore wave frequency, intensity or a combination thereof are selected to maintain a difference between a maximum and minimum pH during day light hours of less than 0.8 pH units, or less than 0.7 pH units, or less than 0.6 pH units, or less than 0.5 pH units, or less than 0.4 pH units, or less than 0.3 pH units. As used herein, the term day light hours refers to one-half hour before an official sunrise through one-half hour after official sunset of the region of operation.

In some embodiments, the wave frequency, intensity or a combination thereof is adjusted using the bore wave generator 11 to disrupt an air-liquid interface of the algae cultivation fluid 12 to induce direct absorption of atmospheric nitrogen from air into the algae cultivation fluid 12 such that a majority of the nitrogen in the algae and/or dissolved in the algae cultivation fluid 12 is from the atmospheric carbon dioxide, or at least 55% is from atmospheric nitrogen, or at least 60%, or at least 65%, or at least 70%, or at least 75%, or at least 80%, or at least 85%, to less than 90%, or less than 95%, or 100% of the nitrogen is from atmospheric nitrogen. In some embodiments, the nitrogen content in the algae or the nitrogen content in the algae cultivation fluid 12 may be measured using methods known to the skilled artisan, such as a CHN analyzer or a gas sensing electrode (e.g., nitrogen sensing electrode).

In some embodiments, the wave frequency, intensity or a combination thereof is adjusted using the bore wave generator 11 to maintain an average nitrogen concentration obtained through the absorption of atmospheric nitrogen. In some embodiments, the wave frequency, intensity or a combination thereof is adjusted to maintain an average nitrogen concentration of at least 1 mg/mL, or at least 5 mg/mL, or at least 10 mg/mL, or at least 15 mg/mL, to less than 20 mg/mL, or less than 25 mg/mL, or less than 30 mg/mL.

In some embodiments, the wave frequency, intensity or a combination thereof is adjusted using the bore wave generator 11 based on an atmospheric light intensity (e.g., increased during high light intensity values, and decreases during low light intensity values). In some embodiments, the one or more measuring device 40 is a light intensity sensor configured to monitor the atmospheric light intensity. In some embodiments, the wave frequency, intensity or a combination thereof is adjusted from 10s to 300s based on measured atmospheric light intensity values. For example, the wave frequency, intensity or a combination thereof may be increased to a high frequency, intensity or a combination thereof (e.g., from 10s to 100s) during high light intensity (e.g., from greater than 200 lux to 120,000 lux) and decreased (e.g., from 100s to 300s) during low light intensity (e.g., from 0.0001 lux to 200 lux).

In some embodiments, the wave frequency, intensity or a combination thereof is adjusted using the bore wave generator 11 based on a desired biomass productivity. In some embodiments, the biomass productivity is measured, and the wave frequency, intensity or a combination thereof is adjusted to maintain a desired set point. In some embodiments, the wave frequency, intensity or a combination thereof is adjusted to maintain a biomass productivity of at least 8 $g/m^2d$, or at least 15 $g/m^2d$, or at least 20 $g/m^2d$, or at least 25 $g/m^2d$, to less than 30 $g/m^2d$, to less than 35 $g/m^2d$, to less than 40 $g/m^2d$, or to less than 45 $g/m^2d$.

In some embodiments, the controller 39 may control a valve in the diffusers 24 to control the rate of diffusion of air into the algae cultivation fluid 12. In some embodiments, the controller 39 has programming stored therein to control the valve to flow air through the diffusers 24 as the bore waves pass over the air-liquid mixing devices 7, and cease air flow once the bore waves have passed over the diffusers 24. In some embodiments, the controller 39 has programming stored therein to control the valve to cease air flow through the diffusers as the bore waves approach the air-liquid mixing devices 7 (e.g., within 1 ft, or 2 ft, or 3 ft, or 4 ft, or 5 ft, or 10 ft, or 15 ft, or more), and resume air flow once the bore waves move away from the diffusers 24 (e.g., at least 0 ft, 1 ft past, or 2 ft, or 3 ft, or 4 ft, or 5 ft, or 10 ft, or 15 ft, or more).

Figure 15:
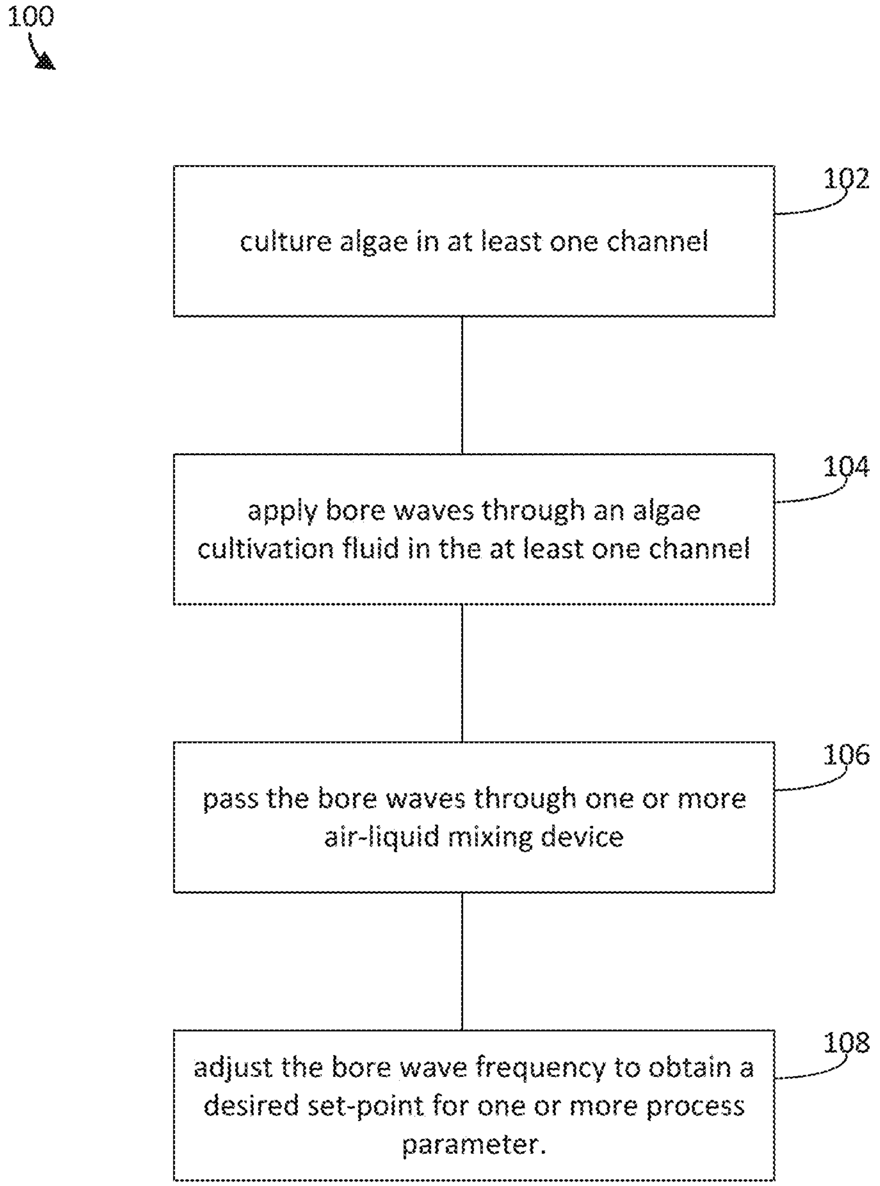
FIG. 15 is a flow chart illustrating exemplary steps of a method in accordance with some embodiments of the present disclosure.

III. Method of Use:

Referring to FIG. 15, a flow chart is provided illustrating an example method 100 of producing algae using an algae cultivation system 1. As indicated by step 102, the method 100 includes culturing algae in at least one channel 2 having a sloped bottom surface 6*a*, 6*b*, opposing side walls 5*a*, 5*b*, and an algae cultivation fluid 12 disposed in the at least one channel 2. The method 100 further includes applying bore waves through the algae cultivation fluid 12 at a bore wave frequency sufficient to disrupt an air-liquid interface of the algae cultivation fluid 12 to induce direct absorption of atmospheric carbon dioxide and/or nitrogen from air into the algae, as indicated in step 104. The method 100 may further include applying the bore waves through one or more air-liquid mixing device 7 configured within the at least one channel 2 to facilitate direct absorption of the carbon dioxide and/or nitrogen into the algae cultivation fluid 12, as indicated in step 106. In some embodiments, the method 100 includes adjusting the bore wave frequency, intensity or a combination thereof to obtain or maintain a desired set-point for one or more process parameter within the algae cultivation system 1, as indicated in step 108. The method 100 may utilize the controller 39 to implement one or more process control action on any one of the algae cultivation systems 1 described herein.

EXAMPLES

The following examples are presented by way of illustration and are not meant to be limiting in any way.

Inventive Example 1

*Spirulina* was cultivated in a 600 $m^2$ raceway with supercritical waves traveling 1.1 m/s. The period for the waves was one every 1.25 minutes. Two cultivation conditions were tested. The first condition was cultivation at pH 9.5 with $NaHCO_3$ added daily to supply the $CO_2$ for cultivation. The second was at pH 10.4 with no added $CO_2$, so that all $CO_2$ for cultivation was from direct air capture. The productivity under the first condition averaged 11.8 $g/m^2d$ and the second condition averaged 12.1 $g/m^2d$, so substantially the same productivity was achieved with and without added $CO_2$.

Inventive Example 2

Figure 16:
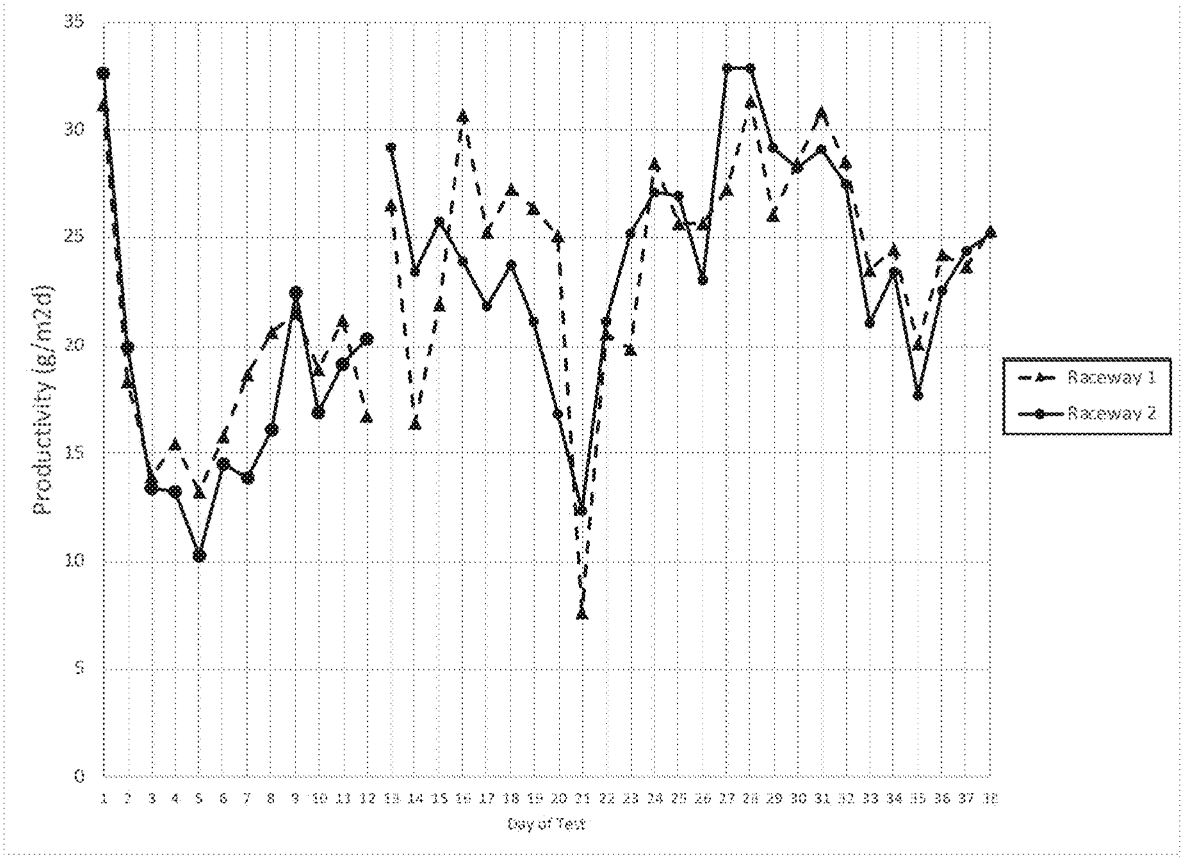
FIG. 16 is a graph of biomass productivity in accordance with some embodiments of the present disclosure.

Two sloped raceways were operated to cultivate *Nitzschia* sp. The equivalent bicarbonate concentration in the cultivation media was 0.3 molar in each raceway. The first raceway was operated at a pH of approximately 9.5, and bicarbonate media was used to supply the $CO_2$ for growth. The second raceway was operated at a pH of approximately 10.5 with a blower and a diffuser to supply air bubbles, and the only $CO_2$ source for growth was the air. The productivity of the two raceways was tracked over 38 days. FIG. 16 presents a plot of the productivity in each of the raceways. The growth rate was similar in each raceway, and the average productivity for the 38 days for each raceway was between 22 and 23 $g/m^2d$.

Inventive Example 3

*Nitzschia* was cultivated in 2 $m^2$ raceways simulating wave mixing with no paddlewheel at an average pH of about 10.4. The concentration of sodium ions added to the media as sodium carbonate varied from 0.01 molar to 0.3 molar. The productivity and pH were measured during cultivation without any added $CO_2$, so that the all $CO_2$ for growth was supplied via direct air capture. Because $CO_2$ is absorbed in the day and night, but only consumed during the day, the pH varied from the lowest value in the early morning to the highest value in the afternoon. The pH swing is the difference between the highest and lowest pH. The following Table 1 summarizes the results. Direct air capture with higher molarity sodium as sodium carbonate/sodium bicarbonate resulted in a higher productivity and smaller pH swing.

TABLE 1

| No+ molarity | Productivity (g/$m^2$d) | pH swing |
|---|---|---|
| 0.01 | 3.8 | 0.83 |
| 0.03 | 5.3 | 0.66 |
| 0.1 | 7.6 | 0.50 |
| 0.3 | 11.2 | 0.37 |

Comparative Example 1

*Spirulina* was cultivated in a 1-acre raceway without waves at a pH of 10.5. The algal productivity with direct air capture without waves was found to be 4 g/$m^2$d. For the same conditions in a large-scale raceway with the bore waves described in Inventive Example 1, the productivity was 12 g/$m^2$d.

The invention has been described according to one or more preferred embodiments, and it should be appreciated that many equivalents, alternatives, variations, and modifications, aside from those expressly stated, are possible and within the scope of the invention.

The preceding discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

It is to be understood that the disclosure is not limited in its application to the details of construction and the arrangement of components set forth in the description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

We claim:

1. A method comprising the steps of:

culturing algae in at least one channel having a bottom surface, opposing side walls coupled to the bottom surface, and an algae cultivation fluid disposed in the at least one channel; and applying bore waves through the algae cultivation fluid at a bore wave frequency sufficient to disrupt an air-liquid interface of the algae cultivation fluid to induce direct absorption of atmospheric carbon dioxide from air into the algae cultivation fluid, wherein the bore wave frequency, a bore wave intensity, or a combination thereof is adjusted to obtain a minimum bicarbonate concentration in the algae cultivation fluid from 1 mM to 150 mM.

2. The method of claim 1, wherein the bore wave frequency, intensity, or a combination thereof is adjusted to obtain a minimum bicarbonate concentration in the algae cultivation fluid from 10 mM to 150 mM.

3. The method of claim 2, wherein an equivalent bicarbonate concentration of sodium ions in the algae cultivation fluid is 10 mM to 500 mM.

4. The method of claim 1 further including measuring at least one process parameter; and adjusting the bore wave frequency, intensity, or a combination thereof based on the at least one parameter or rate of change of the at least one parameter.

5. The method of claim 4, wherein the at least one process parameter is selected from the group consisting of a pH, a dissolved oxygen content, a bicarbonate concentration, a nitrogen concentration, solar intensity, algae growth rate, turbidity, optical density, and temperature.

6. The method of claim 4 further including adjusting the bore wave frequency, intensity, or a combination thereof to maintain a user-defined set-point of the at least one process parameter.

7. The method of claim 1, wherein a majority of the carbon or nitrogen in the algae is from the atmospheric carbon dioxide or atmospheric nitrogen.

8. The method of claim 1, wherein the bottom surface of the channel is sloped.

9. The method of claim 8, wherein the slope of the bottom surface is less than 0.5%.

10. The method of claim 1, wherein the at least one channel includes from one air-liquid mixing device for every 300 $ft^2$ of surface of the at least one channel to one air-liquid mixing device for every 400,000 $ft^2$ of surface of the at least one channel.

11. The method of claim 1, wherein one or more air-liquid mixing devices are powered by a flow of the bore waves.

12. The method of claim 1, wherein a rate of air-liquid mixing is adjusted during the cultivation to reduce energy consumption.

13. The method of claim 12, wherein solar energy is used to power one or more air-liquid mixing devices, and wherein a rate of air-liquid mixing is greater during times of higher solar radiation relative to times of lower solar radiation.

14. The method of claim 1, wherein an air-liquid mixing device generates air bubbles in the algae cultivation fluid.

15. The method of claim 14, wherein a bubble generation rate is increased when the bore wave passes the air-liquid mixing device, and is decreased during a period in between the bore waves.

16. The method of claim 1, wherein the at least one channel has a surface area of at least 100 $ft^{2.}$

17. The method of claim 1, wherein the at least one channel has a surface area from 10,000 $ft^2$ to 20,000,000 $ft^{2.}$ 18. A method comprising the steps of:

culturing algae in at least one channel having a bottom surface, opposing side walls coupled to the bottom surface, and an algae cultivation fluid disposed in the at least one channel; and applying bore waves through the algae cultivation fluid at a bore wave frequency sufficient to disrupt an air-liquid interface of the algae cultivation fluid to induce direct absorption of atmospheric carbon dioxide from air into the algae cultivation fluid, wherein an equivalent bicarbonate concentration of sodium ions in the algae cultivation fluid and the bore wave frequency are selected to maintain a difference between a maximum and minimum pH during day light hours of less than 0.8 pH units.

19. The method of claim 18, wherein an equivalent bicarbonate concentration of sodium ions in the algae cultivation fluid and the bore wave frequency are selected to maintain a difference between a maximum and minimum pH during day light hours of less than 0.5 pH units.

20. A method comprising the steps of:

culturing algae in at least one channel having a bottom surface, opposing side walls coupled to the bottom surface, and an algae cultivation fluid disposed in the at least one channel; and applying bore waves through the algae cultivation fluid at a bore wave frequency sufficient to disrupt an air-liquid interface of the algae cultivation fluid to induce direct absorption of atmospheric carbon dioxide from air into the algae cultivation fluid, wherein the bore wave frequency, a bore wave intensity, or a combination thereof is adjusted to maintain a pH in the algae cultivation fluid of less than 11.

21. The method of claim 20, further adjusting the bore wave frequency, intensity, or a combination thereof to maintain a pH in the algae cultivation fluid of less than 10.6.

22. The method of claim 20, further adjusting the bore wave frequency, intensity, or a combination thereof to maintain a pH in the algae cultivation fluid of less than 10.2.

23. The method of claim 20, wherein the bore wave frequency is adjusted by displacing a gate in a bore wave generator.

24. The method of claim 23 further including displacing the gate at a frequency from 10 seconds to 300 seconds to apply the bore waves through the algae cultivation fluid.

25. The method of claim 20, wherein the bore wave intensity is adjusted by a height of the algae cultivation fluid behind a gate in a bore wave generator.

26. The method of claim 25, wherein the height of algae cultivation fluid is adjusted by a rate of filling of an area behind the gate with algae cultivation fluid.

* * * * *

UNITED STATES PATENT AND TRADEMARK OFFICE

CERTIFICATE OF CORRECTION

PATENT NO. : 12,426,556 B2
APPLICATION NO. : 17/346030
DATED : September 30, 2025
INVENTOR(S) : David A. Hazlebeck et al.

It is certified that error appears in the above-identified patent and that said Letters Patent is hereby corrected as shown below:

In the Specification

Table 1, Column 21, Line 8, "No+" should be --Na+--.

Signed and Sealed this
Ninth Day of December, 2025

John A. Squires
*Director of the United States Patent and Trademark Office*